United States Patent [19]

Bennett

[11] 4,228,280
[45] Oct. 14, 1980

[54] PYRANO[4,3-e]-AS-TRIAZINES AND CORRESPONDING 4-OXIDES

[75] Inventor: Gregory B. Bennett, Mendham, N.J.

[73] Assignee: Sandoz, Inc., E. Hanover, N.J.

[21] Appl. No.: 39,659

[22] Filed: May 16, 1979

Related U.S. Application Data

[63] Continuation-in-part of Ser. No. 874,940, Feb. 3, 1978, abandoned, which is a continuation-in-part of Ser. No. 779,071, Mar. 18, 1977, abandoned.

[51] Int. Cl.² ........................................... C07D 491/08
[52] U.S. Cl. .................................................... 544/184
[58] Field of Search ........................................ 544/184

[56] References Cited

U.S. PATENT DOCUMENTS

| | | | |
|---|---|---|---|
| 3,962,240 | 6/1976 | Bennett | 544/184 |
| 3,963,713 | 6/1976 | Bennett | 544/184 |

OTHER PUBLICATIONS

Neunhoeffer et al., "Chemistry of 1,2,3-Triazines and 1,2,4-Triazines, Tetrazines, and Pentazines", Interscience Publication, John Wiley & Sons, New York (1978) pp. 750-751.

*Primary Examiner*—John M. Ford
*Attorney, Agent, or Firm*—Gerald D. Sharkin; Robert S. Honor; Timothy G. Rothwell

[57] ABSTRACT

This disclosure describes novel compounds of the formula

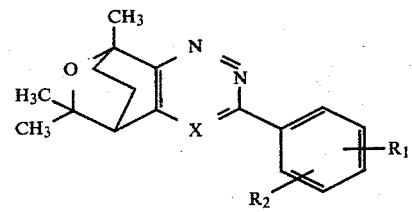

wherein
$R_1$ and $R_2$ each independently represent hydrogen, halo having an atomic weight of about 19 to 36, lower alkyl, straight chain lower alkoxy, amino, nitro or trifluoromethyl, and
X represents

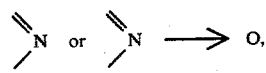

which are useful as minor tranquilizers and sleep inducers.

26 Claims, No Drawings

PYRANO[4,3-e]-AS-TRIAZINES AND CORRESPONDING 4-OXIDES

This application is a continuation-in-part of copending application Ser. No. 874,940, filed Feb. 3, 1978, now abandoned which in turn is a continuation-in-part of copending application Ser. No. 779,071, filed Mar. 18, 1977, now abandoned.

This invention relates to 3-substituted or unsubstituted phenyl-5,8-dihydro-6,6,8-trimethyl-5,8-ethano-6H-pyrano[4,3-e]-as-triazines and corresponding 4-oxides which exhibit minor tranquilizer and sleep inducer activity. In particular, it relates to pyrano[4,3-e]-as-triazines and corresponding 4-oxides, pharmaceutically acceptable salts, their preparation and intermediates thereof.

The compounds of this invention may be represented by the following structural formula:

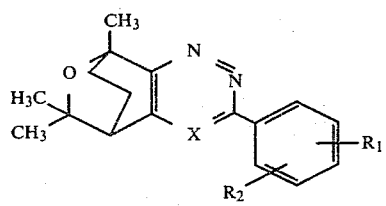

wherein
$R_1$ and $R_2$ each independently represent hydrogen, halogen having an atomic weight of about 19 to 36, lower alkyl, i.e., alkyl having 1 to 4 carbon atoms, e.g., methyl, ethyl, isopropyl and the like, straight chain lower alkoxy, i.e., alkoxy having 1 to 4 carbon atoms, e.g., methoxy, ethoxy and the like, amino, nitro or trifluoromethyl, and
X represents

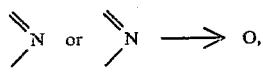

provided that
(i) when one of $R_1$ and $R_2$ represents nitro, the other is other than nitro or trifluoromethyl;
(ii) when $R_1$ and $R_2$ represent trifluoromethyl, they are on other than adjacent carbon atoms; an
(iii) when $R_1$ and $R_2$ represent t-butyl, they are on other than adjacent carbon atoms; and
(iv) when one of $R_1$ and $R_2$ is trifluoromethyl and the other is t-butyl, they are on other than adjacent carbon atoms.

The compounds of formula (I) in which X represents

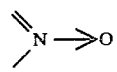

may be prepared according to the following reaction scheme:

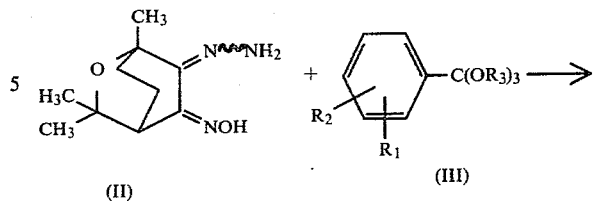

where
$R_3$ represents lower alkyl having 1 to 2 carbon atoms, i.e., methyl or ethyl, and
$R_1$, $R_2$ and the provisos are as defined above.

The compounds of formula (Ia) are prepared by treating a compound of the formula (II) with a compound of the formula (III) in the presence of an inert atmosphere, e.g., nitrogen, helium or argon and in the presence of an inert organic solvent. Although the particular solvent employed is not critical, the preferred solvents include the aromatic hydrocarbons such as benzene, toluene and the like, the lower alkanols such as methanol, ethanol and the like, or an excess of the ortho ester of formula (III), the latter being especially preferred. The temperature of the reaction is not critical, but it is preferred that the reaction be run from about 70° to 200° C., preferably from about 130° to 150° C. The reaction is run from about 12 to 36 hours, preferably from about 15 to 20 hours. The product is recovered using conventional techniques, e.g., filtration.

Another aspect of this invention and the preferred method of preparing the compounds of formula (I) in which X represents

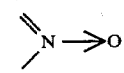

and one of $R_1$ and $R_2$ is nitro and the other is other than nitro or trifluoromethyl may be illustrated by the following reaction scheme:

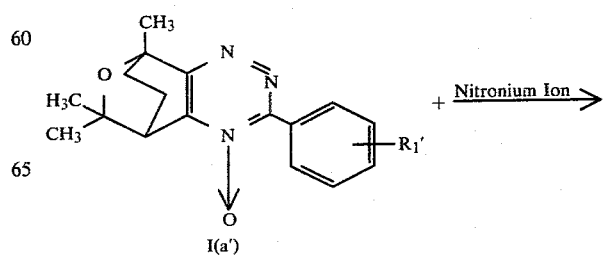

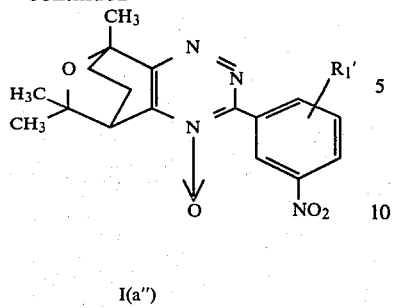

I(a")

where
R$_1'$ is hydrogen, halo having an atomic weight of about 19 to 36, lower alkyl, i.e., alkyl having 1 to 4 carbon atoms, e.g., methyl, ethyl and the like, straight chain lower alkoxy, i.e., alkoxy having 1 to 4 carbon atoms, e.g., methoxy, ethoxy and the like, or amino.

The compounds of formula I(a") may be prepared by treating a compound of formula I(a') with a nitronium ion-forming reactant in the presence of an inert organic solvent. The nitronium ion-forming reactant may be prepared, for example, from a mixture of sulfuric acid and nitric acid, a mixture of trifluoromethanesulfonic acid with fuming nitric acid, or a mixture of hydrogen fluoride, and dinitrogen peroxide in nitromethane at −20° C. saturated with boron fluoride, preferably trifluoromethane sulfonic acid with fuming nitric acid, in a ratio of 2 moles trifluoromethanesulfonic acid to one mole of fuming nitric acid. Although the particular solvent used is not critical, the preferred solvents include the aromatic hydrocarbons such as benzene, toluene and the like or the halogenated hydrocarbons such as methylene chloride chloroform and the like, preferably methylene chloride. The temperature of the reaction is not critical, but it is preferred that the reaction be run from about −80° C. to +70° C., preferably from about −35° C. to +30° C. The reaction is run from about 19 to 96 hours, preferably from about 60 to 75 hours. The product is recovered using conventional techniques, e.g., recrystallization.

The compounds of formula (I) in which X represents

may be prepared according to the following reaction scheme:

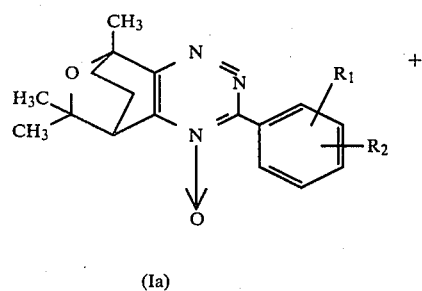

(Ia)

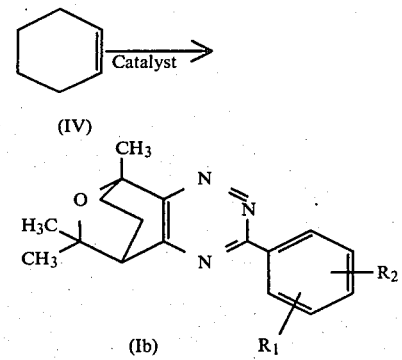

(IV)

(Ib)

where R$_1$, R$_2$ and the provisos are as defined above.

The compounds of formula (Ib) are prepared by treating a compound of the formula (Ia) with cyclohexene (IV) in an inert atmosphere, e.g., nitrogen, helium, or argon, preferably nitrogen, and in the presence of a noble metal catalyst such as palladium, platinum, rhodium and the like, preferably palladium, optionally neat or on a support such as charcoal, in an inert organic solvent. Although the particular solvent used is not critical, it is preferred that the reaction be carried out in the presence of the lower alkanols, e.g., methanol, ethanol, and the like, preferably ethanol. Temperature of the reaction is not critical but it is preferred that the reaction be carried out between 20° to 200° C., preferably from about 70° to 110° C. The reaction is run from about 5 to 72 hours, preferably from about 15 to 30 hours. The product is recovered using conventional techniques, e.g., crystallization.

The compounds of formula (II) may be prepared according to the following reaction scheme:

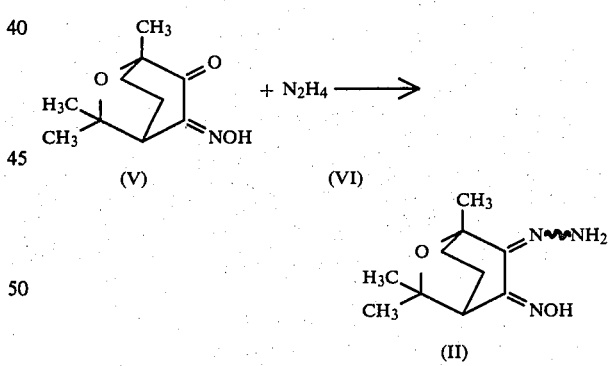

The compounds of formula (II) are prepared by treating a compound of the formula (V) with hydrazine (VI) in an inert atmosphere, e.g., nitrogen, helium or argon, preferably nitrogen in the presence of an inert organic solvent. Although the particular solvent employed is not critical, it is preferred that the reaction be carried out in the presence of the lower alkanols, e.g., methanol, ethanol and the like, preferably ethanol. The temperature of the reaction is not critical, but it is preferred that the reaction be carried out between 0° to 150° C., preferably from about 75° to 85° C. The reaction is run from about 1 to 18 hours, preferably from about 2 to 8 hours. The product is recovered using conventional techniques, e.g., crystallization.

Another preferred aspect of this invention concerns a process for preparing certain of the compounds of formula (I) in accordance with the following reaction scheme:

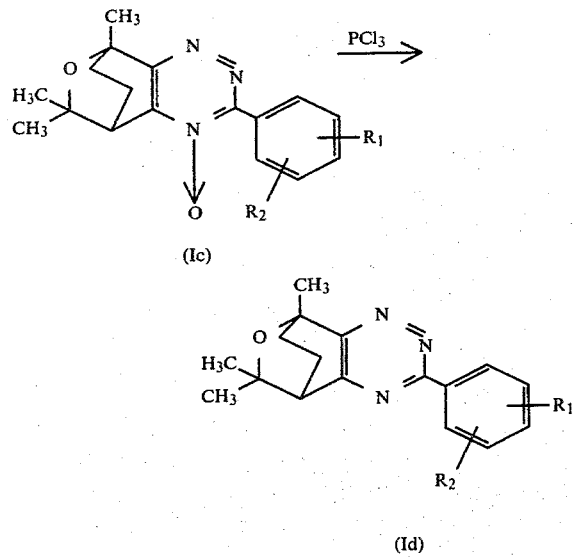

wherein $R_1$, $R_2$ and the provisos are as defined above.

The compounds of formula (Id) are prepared by reacting a compound of the formula (Ic) with phosphorous trichloride in the presence of an inert atmosphere, e.g., nitrogen, helium or argon and in the presence of an inert organic solvent. The particular solvent employed is not critical, however, it is preferred that the reaction be run in the presence of chloroform, tetrachloroethane or 1,2-dichloroethane, the latter being especially preferred. The temperature of the reaction is not critical, but it is preferred that the reaction be run from 50° to 150° C., preferably the reflux temperature of the solvent. The reaction is run from about 4 to 18 hours, preferably from about 6 to 9 hours. The product is recovered using conventional techniques, e.g., recrystallization.

The compounds of formula (Ic) are prepared in accordance with the following reaction scheme:

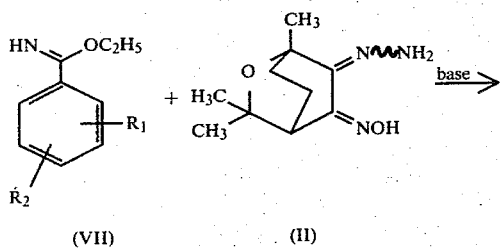

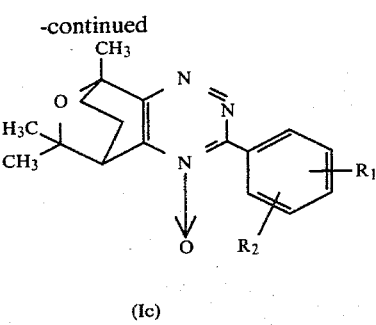

wherein $R_1$, $R_2$ and the proviso are as defined above.

The compounds of formula (Ic) are prepared by reacting a compound of the formula (VII) with a compound of the formula (II) in the presence of a base such as sodium carbonate, potassium carbonate, sodium hydroxide, potassium hydroxide and the like, preferably potassium carbonate and in the presence of an inert organic solvent. Although the particular solvent used is not critical, the preferred solvents include the aromatic hydrocarbons such as benzene, toluene and the like, preferably toluene. The temperature of the reaction is not critical, but it is preferred that the reaction be run from about 75° to 150° C., preferably the reflux temperature of the solvent. The reaction is run from about 3 to 15 hours, preferably from about 4 to 6 hours. The product is recovered using conventional techniques, e.g., recrystallization.

Certain of the compounds of formulae (III), (IV), (V), (VI) and (VII) are known and may be prepared by methods described in the literature. Those compounds of formulae (III), (IV), (V), (VI) and (VII) not specifically disclosed may be prepared by analogous methods from known starting materials.

It will be understood that the compounds of formula (I) may exist in the form of optically active isomers and can be separated and recovered by conventional techniques, and that such isomeric forms are included within the scope of this invention. They also can be prepared starting with one of the optically active isomers of compound (II). The following isomers have been separated and recovered and represent a preferred embodiment of this invention:

(a) (+)-3-(m-trifluoromethylphenyl)-5,8-dihydro-6,6,8-trimethyl-5,8-ethano-6H-pyrano[4,3-e]-as-triazine-4-oxide,
(b) (+)-3-(m-trifluoromethylphenyl)-5,8-dihydro-6,6,8-trimethyl-5,8-ethano-6H-pyrano[4,3-e]-as-triazine,
(c) (+)-3-(m-nitrophenyl)-5,8-dihydro-6,6,8-trimethyl-5,8-ethano-6H-pyrano[4,3-e]-as-triazine-4-oxide,
(d) (+)-3-(m-nitrophenyl)-5,8-dihydro-6,6,8-trimethyl-5,8-ethano-6H-pyrano[4,3-e]-as-triazine,
(e) (−)-3-(m-nitrophenyl)-5,8-dihydro-6,6,8-trimethyl-5,8-ethano-6H-pyrano[4,3-e]-as-triazine-4-oxide, or
(f) (−)-3-(m-nitrophenyl)-5,8-dihydro-6,6,8-trimethyl-5,8-ethano-6H-pyrano[4,3-e]-as-triazine.

The compounds which are particularly preferred are compounds (a) and (f) set out above.

The compounds of formula (I) are useful because they possess pharmacological activity in animals as sleep inducers and minor tranquilizers as indicated (1) by the hexobarbital reinduction method of Winter, J. Pharmacol. and Exp. Therap., 94, 7-11, 1948; (2) by their ability to produce docility in behavior tests in mice given 10 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (3) by their ability to antagonize chronic convulsions and death in mice given 20 to 250 mg/kg i.p. of N-sulfamoylazepine; (4) by scoring for loss of righting reflex according to the method of Reed-Muench (American Journal of Hygiene, 27: 493–497, 1938), in which mice are administered 12.5 mg/kg, i.p. Thioridazine, immediately after which test compound is administered at dosages of 5 to 100 mg/kg in a volume of 0.1 ml/10 g. body weight. Sixty minutes after dosing, the mice are scored for loss of right reflex; (5) in the Cebus monkey using chronically implanted electrodes. Brain readings are obtained via a ten or sixteen channel electroencephalograph. For the recording sessions, the monkeys are restrained by neck and waist plates in chairs in full side observation cages, at the same time every night, for thirteen and one half hours, Monday through Thursday. Gross behavior is monitored via closed circuit television and video tape recordings. The compounds of formula (I) are administered p.o. immediately on placing the monkey in the observation cages with at least seven days intervening between drug administration. Physiological saline is administered via a similar route and at the same time on all control runs. Control data are collected at least three days per week and accumulated to give control data for fifteen sessions per monkey. Data from each session are statistically compared via computer analysis to the previous 5–15 control sessions for the particular animal, with particular emphasis being given to the following phases of the sleep-wakefulness cycle: resting awake, light sleep, deep sleep, paradoxical (REM) sleep, "pseudo-" paradoxical sleep, latency to onset of deep sleep, and latency to onset of first epoch of paradoxical sleep; and (6) by their ability to reduce conflicts as defined in the Gellar Conflict Test [Irving Geller, Psychopharmacologia, I, 42–492, (1960)].

The sleep inducing effective dosage of the compounds of formula (I) will vary depending on the particular compound employed. However, in general, satisfactory results are obtained when the compounds are administered orally at a daily dosage of from about 0.1 milligram to about 75 milligrams per kilogram of animal body weight, typically given in a single dose at bedtime. For most large mammals, the total daily dosage is from about 1 to about 300 milligrams, preferably at bedtime and dosage forms suitable for internal administration comprise from about 0.25 to about 150 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use, the effective dosage will vary depending on the particular compound employed. However, in general, satisfactory results are obtained when the compounds are administered orally at a daily dosage of from about 1.0 milligram to about 75 milligrams per kilogram of animal body weight, typically given in divided doses two to four times per day. For most large mammals, the total daily dosage is from about 5 to 500 milligrams, and dosage forms suitable for internal administration comprise from about 1.25 to about 250 milligrams of the compound in admixture with a solid or liquid pharamceutical carrier or diluent.

For the uses mentioned above, the compound may be administered orally in such forms as tablets, capsules, elixirs, suspensions and the like, or parenterally in the form of injectable solutions or suspensions. The dosage will vary depending upon the mode of administration utilized and the compound employed.

The compounds of formula (I) may be similarly administered in the form of their non-toxic pharmaceutically acceptable salts. Such salts possess the same order of activity as the free base and are readily prepared by reacting the base with an appropriate acid by conventional technique and, accordingly, are included within the scope of this invention. Representative of such salts are the mineral acid salts, e.g., hydrochloride, hydrobromide, sulfate and the like, and the organic acid salts such as succinate, benzoate, maleate and the like.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers in divided doses two to four times per day.

| Ingredients | Weight (mg.) Tablet | Capsule |
| --- | --- | --- |
| 3-phenyl-5,8-dihydro-6,6,8-trimethyl-5,8-ethano-6H-pyrano [4,3-e]-as-triazine | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

1,3,3-Trimethyl-2-oxabicyclo[2,2,2]octan-5,6-dione-5-oxime-6hydrazone

A mixture of 1.97 g. (0.01 mole) 1,3,3-trimethyl-2-oxabicyclo[2,2,2]octan-5,6-dione-5-oxime and 0.35 ml. (0.011 mole) anhydrous hydrazine (98%) in 25 ml. absolute ethanol is refluxed under nitrogen at a bath temperature of 80° C. for 1 hour. After evaporation of the solvent, the residue is recrystallized from ether to give 1,3,3-trimethyl-2-oxabicyclo [2,2,2]octan-5,6-dione-5-oxime-6-hydrazone; mp. 138° to 142° C.

EXAMPLE 2

3-Phenyl-5,8-dihydro-6,6,8-trimethyl-5,8-ethano-6H-pyrano [4,3-e]-as-triazine-4-oxide A solution of 2.11 g. (0.01 mole) 1,3,3-trimethyl-2-oxabicyclo[2,2,2]octan-5,6-dione-5-oxime-6-hydrazone in 10 ml. trimethylorthobenzoate is refluxed under nitrogen for 18 hours at a bath temperature of 140° C. during which time all distillate is removed. The resulting mixture is cooled and evaporated to dryness in vacuo. After filtering the residue dissolved in 2% methanol-chloroform through silica gel, and evaporation of the filtrate the resulting solid is triturated with ether, giving 3-phenyl-5,8-dihydro-6,6,8-trimethyl-5,8-ethano-6H-pyrano [4,3-e]-as-triazine-4-oxide; m.p. 186.5° to 189° C.

Following the above procedure and using in place of trimethylorthobenzoate an equivalent amount of
(a) p-chloro-trimethylorthobenzoate, (b) p-fluoro-trimethylorthobenzoate,
(c) p-methyl-trimethylorthobenzoate,
(d) p-methoxy-trimethylorthobenzoate,
(e) m-trifluoromethyl-trimethylorthobenzoate,
(f) p-amino-trimethylorthobenzoate,
(g) p-nitro-trimethylorthobenzoate,
(h) m-nitro-trimethylorthobenzoate,
(i) m-chloro-trimethylorthobenzoate, or
(j) 3,4-dimethoxy-trimethylorthobenzoate,
there is obtained (a) 3-(p-chlorophenyl)-5,8-dihydro-6,6,8-trimethyl-5,8-ethano-6H-pyrano[4,3-e]-as-triazine-4-oxide,
(b) 3-(p-fluorophenyl)-5,8-dihydro-6,6,8-trimethyl-5,8-ethano-6H-pyrano[4,3-e]-as-triazine-4-oxide,
(c) 3-(p-tolyl)-5,8-dihydro-6,6,8-trimethyl-5,8-ethano-6H-pyrano[4,3-e]-as-triazine-4-oxide,
(d) 3-(p-anisyl)-5,8-dihydro-6,6,8-trimethyl-5,8-ethano-6H-pyrano[4,3-e]-as-triazine-4-oxide,
(e) 3-(m-trifluoromethylphenyl)-5,8-dihydro-6,6,8-trimethyl-5,8-ethano-6H-pyrano[4,3-e]-as-triazine-4-oxide,
(f) 3-(p-aminophenyl)-5,8-dihydro-6,6,8-trimethyl-5,8-ethano-6H-pyrano[4,3-e]-as-triazine-4-oxide,
(g) 3-(p-nitrophenyl)-5,8-dihydro-6,6,8-trimethyl-5,8-ethano-6H-pyrano[4,3-e]-as-triazine-4-oxide,
(h) 3-(m-nitrophenyl)-5,8-dihydro-6,6,8-trimethyl-5,8-ethano-6H-pyrano[4,3-e]-as-triazine-4-oxide,
(i) 3-(m-chlorophenyl)-5,8-dihydro-6,6,8-trimethyl-5,8-ethano-6H-pyrano[4,3-e]-as-triazine-4-oxide, or
(j) 3-(3,4-dimethoxyphenyl)-5,8-dihydro-6,6,8-trimethyl-5,8-ethano-6H-pyrano[4,3-e]-as-triazine-4-oxide, respectively.

EXAMPLE 3

3-Phenyl-5,8-dihydro-6,6,8-trimethyl-5,8-ethano-6H-pyrano [4,3-e]-as-triazine

To a solution of 1.80 g. (0.006 mole) 3-phenyl-5,8-dihydro-6,6,8-trimethyl-5,8-ethano-6H-pyrano[4,3-e]-as-triazine-4-oxide and 1.50 g. (0.018 mole) cyclohexene in 30 ml. absolute ethanol there is added 60 mg. 10% palladium on charcoal. The resulting mixture is refluxed under a nitrogen atmosphere for 18 hours. The catalyst is then removed by filtration and the filtrate evaporated to give 3-phenyl-5,8-dihydro-6,6,8-trimethyl-5,8-ethano-6H-pyrano[4,3-e]-as-triazine; m.p. 180° to 189° C.

Following the above procedure and using in place of 3-phenyl-5,8-dihydro-6,6,8-trimethyl-5,8-ethano-6H-pyrano[4,3-e]-as-triazine-4-oxide an equivalent amount of
(a) 3-(p-chlorophenyl)-5,8-dihydro-6,6,8-trimethyl-5,8-ethano-6H-pyrano[4,3-e]-as-triazine-4-oxide,
(b) 3-(p-fluorophenyl)-5,8-dihydro-6,6,8-trimethyl-5,8-ethano-6H-pyrano[4,3-e]-as-triazine-4-oxide,
(c) 3-(p-tolyl)-5,8-dihydro-6,6,8-trimethyl-5,8-ethano-6H-pyrano[4,3-e]-as-triazine-4-oxide,
(d) 3-(p-anisyl)-5,8-dihydro-6,6,8-trimethyl-5,8-ethano-6H-pyrano[4,3-e]-as-triazine-4-oxide,
(e) 3-(m-trifluoromethylphenyl)-5,8-dihydro-6,6,8-trimethyl-5,8-ethano-6H-pyrano[4,3-e]-as-triazine-4-oxide,
(f) 3-(p-aminophenyl)-5,8-dihydro-6,6,8-trimethyl-5,8-ethano-6H-pyrano[4,3-e]-as-triazine-4-oxide,
(g) 3-(p-nitrophenyl)-5,8-dihydro-6,6,8-trimethyl-5,8-ethano-6H-pyrano[4,3-e]-as-triazine-4-oxide,
(h) 3-(m-nitrophenyl)-5,8-dihydro-6,6,8-trimethyl-5,8-ethano-6H-pyrano[4,3-e]-as-triazine-4-oxide,
(i) 3-(m-chlorophenyl)-5,8-dihydro-6,6,8-trimethyl-5,8-ethano-6H-pyrano[4,3-e]-as-triazine-4-oxide, or
(j) 3-(3,4-dimethoxyphenyl)-5,8-dihydro-6,6,8-trimethyl-5,8-ethano-6H-pyrano[4,3-e]-as-triazine-4-oxide,
there is obtained (a) 3-(p-chlorophenyl)-5,8-dihydro-6,6,8-trimethyl-5,8-ethano-6H-pyrano[4,3-e]-as-triazine,
(b) 3-(p-fluorophenyl)-5,8-dihydro-6,6,8-trimethyl-5,8-ethano-6H-pyrano[4,3-e]-as-triazine,
(c) 3-(p-tolyl)-5,8-dihydro-6,6,8-trimethyl-5,8-ethano-6H-pyrano[4,3-e]-as-triazine,
(d) 3-(p-anisyl)-5,8-dihydro-6,6,8-trimethyl-5,8-ethano-6H-pyrano[4,3-e]-as-triazine,
(e) 3-(m-trifluoromethylphenyl)-5,8-dihydro-6,6,8-trimethyl-5,8-ethano-6H-pyrano[4,3-e]-as-triazine,
(f) 3-(p-aminophenyl)-5,8-dihydro-6,6,8-trimethyl-5,8-ethano-6H-pyrano[4,3-e]-as-triazine,
(g) 3-(p-nitrophenyl)-5,8-dihydro-6,6,8-trimethyl-5,8-ethano-6H-pyrano[4,3-e]-as-triazine,
(h) 3-(m-nitrophenyl)-5,8-dihydro-6,6,8-trimethyl-5,8-ethano-6H-pyrano[4,3-e]-as-triazine,
(i) 3-(m-chlorophenyl)-5,8-dihydro-6,6,8-trimethyl-5,8-ethano-6H-pyrano[4,3-e]-as-triazine, or
(j) 3-(3,4-dimethoxyphenyl)-5,8-dihydro-6,6,8-trimethyl-5,8-ethano-6H-pyrano[4,3-e]-as-triazine, respectively.

EXAMPLE 4

3-(m-nitrophenyl)-5,8-dihydro-6,6,8-trimethyl-5,8-ethano-6H-pyrano[4,3-e]-as-triazine-4-oxide To a mixture of 0.2 ml. (0.005 mole) fuming nitric acid and 1.5 g. (0.01 mole) trifluoromethanesulfonic acid in 15 ml. anhydrous methylene chloride maintained at a temperature of −30° C. there is added dropwise a solution of 0.60 g. (0.002 mole) 3-phenyl-5,8-dihydro-6,6,8-trimethyl-5,8-ethano-6H-pyrano[4,3-e]-as-triazine-4-oxide in 15 ml. methylene chloride, maintaining the temperature at −30° C. throughout the addition. The resulting mixture is allowed to stir at ambient temperature for 72 hours, then poured onto ice and neutralized with solid sodium bicarbonate. The organic layer is removed, washed with saturated brine solution, dried over magnesium sulfate and evaporated. Trituration of the resulting residue with ether gives 3-(m-nitrophenyl)-5,8-dihydro-6,6,8-trimethyl-5,8-ethano-6H-pyrano[4,3-e]-as-triazine-4-oxide-monohydrate; m.p. 150° (d).

Following the above procedure but using in place of 3-phenyl-5,8-dihydro-6,6,8-trimethyl-5,8-ethano-6H-pyrano[4,3-e]-as-triazine-4-oxide, an equivalent amount of
(a) 3-(p-tolyl)-5,8-dihydro-6,6,8-trimethyl-5,8-ethano-6H-pyrano[4,3-e]-as-triazine-4-oxide, or
(b) 3-(p-anisyl)-5,8-dihydro-6,6,8-trimethyl-5,8-ethano-6H-pyrano[4,3-e]-as-triazine-4-oxide
there is obtained
(a) 3-(4-methyl-3-nitrophenyl)-5,8-dihydro-6,6,8-trimethyl-5,8-ethano-6H-pyrano[4,3-e]-as-triazine-4-oxide, or
(b) 3-(4-methoxy-3-nitrophenyl)-5,8-dihydro-6,6,8-trimethyl-5,8-ethano-6H-pyrano[4,3-e]-as-triazine-4-oxide, respectively.

The 3-(m-nitrophenyl)-5,8-dihydro-6,6,8-trimethyl-5,8-ethano-6H-pyrano[4,3-e]-as-triazine-4-oxide of this example is a particularly effective sleep inducer when orally administered to an animal in need of said treatment at a dosage of 200 mg. just before bedtime.

EXAMPLE 5

(−)-3-(m-nitrophenyl)-5,8-dihydro-6,6,8-trimethyl-5,8-ethano-6H-pyrano[4,3-e]-as-triazine (a) Preparation of (+)-3-(m-nitrophenyl)-5,8-dihydro-6,6,8-trimethyl-5,8-ethano-6H-pyrano[4,3-e]-as-triazine-4-oxide To a flask equipped with a reflux condenser, there is added 10.2 g. (0.048 mole) of 3-nitro-benzenecarboximidic acid ethyl ester hydrochloride, 11.7 g. (0.048 mole) of (+)-1,3,3-trimethyl-2-oxabicyclo[2,2,2]octan-5,6-dione-5-oxime-6-hydrazone, 3.6 g. (0.024 mole) of potassium carbonate and 300 ml. of toluene. The resulting mixture is refluxed for 5 hours, then cooled to room temperature. The excess solvent is then removed at reduced pressure on a rotary evaporator. Methylene chloride is then added to dissolve the product and the resulting solution is then filtered. The filtrate is then evaporated and the residue recrystallized from absolute ethanol to yield (+)-3-(m-nitrophenyl)-5,8-dihydro-6,6,8-ethano-6H-pyrano[4,3-e]-as-triazine-4-oxide; m.p. 217.5° C. to 218.5° C.; ORD+7.8°.

(b) (−)-3-(m-nitrophenyl)-5,8-dihydro-6,6,8-trimethyl-5,8-ethano-6H-pyrano[4,3-e]-as-triazine To a flask equipped with stirrer, reflux condenser and gas inlet there is added under nitrogen a mixture of 6.9 g. (0.020 mole) of (+)-3-(m-nitrophenyl)-5,8-dihydro-6,6,8-trimethyl-5,8-ethano-6H-pyrano[4,3-e]-as-triazine-4-oxide, 20 ml. (0.23 mole) of phosphorous trichloride in 300 ml. of 1,2-dichloroethane. The resulting mixture is refluxed for 6.5 hours and then cooled to room temperature, and poured into a beaker containing 500 g. of ice. To this mixture there is added cautiously 60 ml. of 50% aqueous sodium hydroxide while maintaining stirring for 1 hour. The resulting mixture is then transferred to a separatory funnel and permitted to separate. The layers are partitioned and the aqueous phase extracted twice with 300 ml. of methylene chloride and the extracts combined with the organic phase. The resulting solution is washed once with brine, dried over anhydrous magnesium sulfate, and then concentrated to yield a residue which is then recrystallized from absolute ethanol to give (−)-3-(m-nitrophenyl)-5,8-dihydro-6,6,8-trimethyl-5,8-ethano-6H-pyrano[4,3-e]-as-triazine; m.p. 184° to 185° C.; ORD-1.8°.

What is claimed is:

1. A compound of the formula

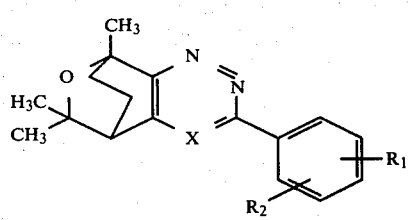

wherein $R_1$ and $R_2$ each independently represent hydrogen, halo having an atomic weight of about 19 to 36, lower alkyl, straight chain lower alkoxy, amino, nitro or trifluoromethyl, and X represents

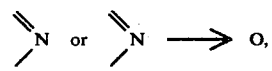

provided that (i) when one of $R_1$ and $R_2$ represents nitro, the other is other than nitro or trifluoromethyl;

(ii) when $R_1$ and $R_2$ represent trifluoromethyl, they are on other than adjacent carbon atoms; and (iii) when $R_1$ and $R_2$ represent t-butyl, they are on other than adjacent carbon atoms, and (iv) when one of $R_1$ and $R_2$ is trifluoromethyl and the other is t-butyl, they are on other than adjacent carbon atoms.

2. A compound of the formula

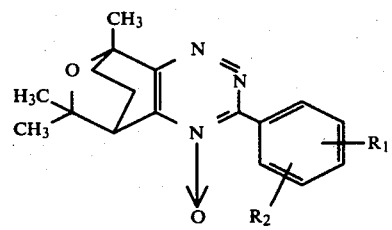

where $R_1$, $R_2$ and the provisos are as defined in claim 1, or a pharmaceutically acceptable salt thereof.

3. A compound of the formula

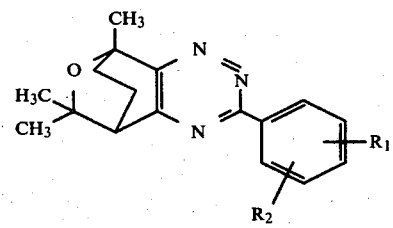

where $R_1$ and $R_2$ and the provisos are as defined in claim 1, or a pharmaceutically acceptable salt thereof.

4. A compound of the formula

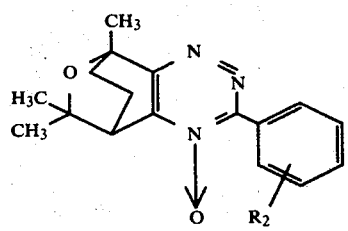

wherein $R_2$ and the provisos are as defined in claim 1, or a pharmaceutically acceptable salt thereof.

5. A compound of the formula

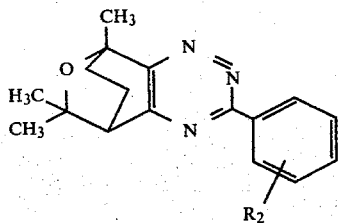

wherein $R_2$ and the provisos are as defined in claim 1, or a pharmaceutically acceptable salt thereof.

6. A compound of the formula

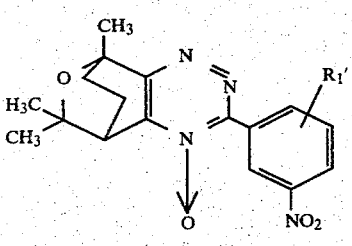

wherein $R_1'$ is hydrogen, halo having an atomic weight of about 19 to 36, lower alkyl, straight chain lower alkoxy, or amino, or a pharmaceutically acceptable salt thereof.

7. A pharmaceutically acceptable salt of a compound of claim 1.

8. A compound of claim 1 which is 3-phenyl-5,8-dihydro-6,6,8-trimethyl-5,8-ethano-6H-pyrano[4,3-e]-as-triazine-4-oxide.

9. The compound of claim 1 which is 3-phenyl-5,8-dihydro-6,6,8-trimethyl-5,8-ethano-6H-pyrano[4,3-e]-as-triazine.

10. The compound of claim 1 which is 3-(m-trifluoromethylphenyl)-5,8-dihydro-6,6,8-trimethyl-5,8-ethano-6H-pyrano[4,3-e]-as-triazine-4-oxide.

11. The compound of claim 1 which is 3-(m-trifluoromethylphenyl)-5,8-dihydro-6,6,8-trimethyl-5,8-ethano-6H-pyrano[4,3-e]-as-triazine.

12. The compound of claim 1 which is 3-(m-nitrophenyl)-5,8-dihydro-6,6,8-trimethyl-5,8-ethano-6H-pyrano[4,3-e]-as-triazine-4-oxide.

13. The compound of claim 1 which is 3-(m-nitrophenyl)-5,8-dihydro-6,6,8-trimethyl-5,8-ethano-6H-pyrano[4,3-e]-as-triazine.

14. The compound of claim 1 which is 3-(p-fluorophenyl)-5,8-dihydro-6,6,8-trimethyl-5,8-ethano-6H-pyrano[4,3-e]-as-triazine-4-oxide.

15. The compound of claim 1 which is 3-(p-fluorophenyl)-5,8-dihydro-6,6,8-trimethyl-5,8-ethano-6H-pyrano[4,3-e]-as-triazine.

16. The compound of claim 1 which is 3-(p-tolyl)-5,8-dihydro-6,6,8-trimethyl-5,8-ethano-6H-pyrano[4,3-e]-as-triazine.

17. The compound of claim 1 which is 3-(p-tolyl)-5,8-dihydro-6,6,8-trimethyl-5,8-ethano-6H-pyrano[4,3-e]as-triazine-4-oxide.

18. The compound of claim 1 which is 3-(p-anisyl)-5,8-dihydro-6,6,8-trimethyl-5,8-ethano-6H-pyrano[4,3-e]as-triazine-4-oxide.

19. The compound of claim 1 which is 3-(m-chlorophenyl)-5,8-dihydro-6,6,8-trimethyl-5,8-ethano-6H-pyrano[4,3-e]as-triazine-4-oxide.

20. A method of inducing sleep which comprises administering a sleep-inducing effective amount of a compound according to claim 1.

21. A metod of treating tension which comprises administering a tranquilizing effective amount of a compound according to claim 1.

22. A pharmaceutical composition comprising a therapeutically effective amount of a compound of claim 1 and a pharmaceutically acceptable diluent or carrier therefor.

23. The compound of claim 1 which is (+)-3-(m-trifluoromethylphenyl)-5,8-dihydro-6,6,8-trimethyl-5,8-ethano-6H-pyrano[4,3-e]-as-triazine.

24. The compound of claim 1 which is (+)-3-(m-trifluoromethylphenyl)-5,8-dihydro-6,6,8-trimethyl-5,8-ethano-6H-pyrano[4,3-e]-as-triazine-4-oxide.

25. The compound of claim 1 which is (−)-3-(m-nitrophenyl)-5,8-dihydro-6,6,8-trimethyl-5,8-ethano-6H-pyrano[4,3-e]-as-triazine.

26. The compound of claim 1 which is (+)-3-(m-nitrophenyl)-5,8-dihydro-6,6,8-trimethyl-5,8-ethano-6H-pyrano[4,3-e]-as-triazine-4-oxide.

* * * * *